United States Patent [19]

Bauer, Jr. et al.

[11] Patent Number: 5,468,899
[45] Date of Patent: Nov. 21, 1995

[54] PROCESS FOR PURIFYING α,β-UNSATURATED ESTERS

[76] Inventors: William Bauer, Jr., 2046 Winthrop Rd., Huntingdon Valley, Pa. 19006; Nelson I. Quiros, 111 Cobbler Ct., Telford, Pa. 18969; Rita K. Upmacis, 560 Riverside Dr., Apt.7-B, New York, N.Y. 10027

[21] Appl. No.: 371,176

[22] Filed: Jan. 11, 1995

[51] Int. Cl.$^6$ .................................................... C07C 67/48
[52] U.S. Cl. ............................................................ 560/218
[58] Field of Search ............................................. 560/218

[56] References Cited

U.S. PATENT DOCUMENTS

| | | | |
|---|---|---|---|
| 4,668,818 | 5/1987 | Lipp et al. | 560/215 |
| 4,748,269 | 5/1988 | Meixner et al. | 560/205 |
| 5,034,558 | 7/1991 | Yoshioka et al. | 560/281 |

FOREIGN PATENT DOCUMENTS

| | | |
|---|---|---|
| 653063 | 11/1962 | Canada . |
| 343583 | 11/1989 | European Pat. Off. . |
| 52-23017 | 2/1977 | Japan . |
| 8183633 | 10/1983 | Japan . |

Primary Examiner—Paul J. Killos
Attorney, Agent, or Firm—R. A. Haggard; T. D. Rogerson

[57] ABSTRACT

This invention provides a method for reducing carbonyl-containing impurities in α,β-unsaturated carboxylic acid esters by treatment of the ester with one or more of a selected phenylenediamine and an acid.

10 Claims, No Drawings

PROCESS FOR PURIFYING α,β-UNSATURATED ESTERS

This invention relates to a method of reducing carbonyl-containing impurities in α,β-unsaturated carboxylic acid esters, particularly in acrylic or methacrylic (hereinafter "(meth)acrylic") esters. Processes for producing such esters which incorporate oxidative steps, such as the vapor phase oxidation of propylene, isobutylene, tertiary butanol, methacrolein, acrolein, or isobutyraldehyde to afford acrylic or methacrylic acid followed by esterification to its respective (meth)acrylic ester, am known to result in product mixtures which contain quantities of carbonyl-containing impurities such as aldehydes and ketones, For example benzaldehyde, furfural, protoanemonin, methacrolein, and acrolein. These impurities are undesirable because they may react with the α,β-unsaturated esters in subsequent reactions, they may interact with other reactants which are intended to react with the esters in subsequent reactions, they may react to form colored impurities, or they may directly inhibit subsequent reactions. In addition, these impurities may interfere with subsequent purification of the ester. For these reasons it is highly desirable to remove these impurities from the ester, particularly from (meth)acrylic esters.

The use of amines for removal of carbonyl impurities such as aldehydes and ketones from α,β-unsaturated acids, such as (meth)acrylic acid, is known. Unfortunately, amines effective for reducing impurities from α,β-unsaturated acids are not necessarily effective for reducing or removing impurities from α,β-unsaturated esters. For example, aniline is highly effective in reducing carbonyl impurities from acrylic acid but has been found to be quite ineffective in reducing impurities in butyl acrylate. One reference, Japanese Kokai No. 52-23017 ("JK017"), discloses a process for purifying (meth)acrylic acids and esters by distilling in the presence of polyamines of type $R^1$—NH—R—NH—$R^2$. This method requires the use of neutral conditions and, when "R" is a phenylenic group, the method is effective only when the amino groups are immediately adjacent one to the other (i.e. in the 1,2, or ortho position). Ortho adjacency is required in the JK017 disclosure because, as taught, the cyclic compound formed between the diamine and a carbonyl impurity cannot result from diaminophenylenes other than from those having the 1,2 relationship. Accordingly, recta- and para-phenylene diamines, for example, are specifically excluded, although it would be advantageous to use diamines such as these because of their low cost and availability.

The problem addressed by the present invention is the reduction of impurities in α,β-unsaturated esters, particularly (meth)acrylic esters, to provide high purity α,β-unsaturated esters in an efficient and low cost process.

We have discovered that carbonyl-containing impurities can be substantially reduced or completely removed from α,β-unsaturated carboxylic acid esters, for example (meth)acrylic esters, by treatment of the ester with one or more selected phenylenediamines in the presence of an acid, typically a mineral acid or a carboxylic acid such as acrylic or methacrylic acid. The treated ester mixture optionally may be subjected to an acid neutralization step with aqueous base, water washing, and distillation. Our discovery provides a new, low cost, simple and effective method for purifying α,β-unsaturated esters. Thus, there is provided a process for purifying an α,β-unsaturated carboxylic acid ester containing carbonyl impurities, comprising a) admixing the α,β-unsaturated carboxylic acid ester containing carbonyl impurities with 1) from 1 to 100 molar ratio of a phenylenediamine, based upon moles of carbonyl impurities, the phenylenediamine having the formulas

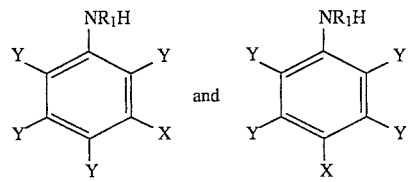

where X is $NR_1R_2$ and $R_1$, $R_2$, and Y are independently selected from hydrogen, $C_1$ to $C_4$ alkyl, phenyl, or naphthyl; and 2) from 1 to 1500 equivalent ratio, based on equivalents of the phenylenediamine, of an acid selected from a $C_1$ to $C_4$ carboxylic acid, a sulfonic acid, phosphoric acid, sulfuric acid, or mixtures thereof, to form a treated ester mixture; and b) holding the treated ester mixture up to 100 hours at a temperature of from 20° C. to 150° C.

The invention also encompasses optional steps of aqueous base neutralizing and aqueous washing the treated ester mixture. The treated ester mixture also may be distilled, with or without the optional acid neutralizing and aqueous washing steps, as a preferred method for isolating substantially carbonyl-free α,β-unsaturated carboxylic acid ester.

DETAILED DESCRIPTION OF THE INVENTION

α,β-Unsaturated carboxylic acid esters (hereafter "esters") which can be purified using this invention include those produced from the $C_3$–$C_{10}$ α,β-unsaturated carboxylic acids, for example, acrylic, methacrylic, 2-butenoic, cyclohexenoic, maleic, or itaconic acid, and the $C_1$–$C_{10}$ alcohols, for example, methanol, ethanol, normal and isopropanol, the butyl alcohols, for example, normal, iso, sec, and tert butanols; cyclohexanol, octanol, ethyl hexanol, glycols, and decanol. Preferred esters are those produced from $C_3$–$C_5$ carboxylic acids and $C_1$–$C_5$ alcohols; more preferred are methyl acrylate, ethyl acrylate, butyl acrylate, methyl methacrylate and butyl methacrylate; of these, most preferred are ethyl acrylate and butyl acrylate because of their commercial importance and large production volume.

The ester may be treated neat or in solution, i.e. dissolved in a water insoluble organic solvent such as an aromatic solvent such as benzene, toluene, xylenes, or ethyl benzene, and hydrocarbon solvents such as n-hexane, n-heptane, or cyclohexane. Preferred solvents include benzene, toluene, and xylene but treatment of neat ester is preferred to avoid solvent use. The order of addition of the phenylenediamine and the acid is not believed critical to the effectiveness of carbonyl impurity removal. The ester can be treated batchwise, that is, by adding the diamine and acid to the ester, mixing with stirring or shaking, and aqueous base treating followed by aqueous washing if desirable, and then distilled if desirable, or it may be treated in a continuous method, that is, by introducing the ester and diamine and acid components into a mixer, continuously mixing them with stirring or shaking, feeding the mixture into a standing vessel where the layers separate, and withdrawing the ester and aqueous layers separately and continuously from the vessel. After separation from the ester, the one or more aqueous solutions may be discarded or used to treat additional ester. The aqueous solution(s) also may be combined with fresh aqueous solution prior to extraction of the ester.

The presence of one or more polymerization inhibitor, for example, hydroquinone (HQ), monomethyl ether of HQ, methylene blue, phenothiazine, copper salicylate, or copper dialkyldithiocarbamates does not adversely affect the process.

A number of amines are not effective in reducing carbonyl-containing impurities in esters; for example, alkyl amines generally have been found relatively ineffective, probably because they are too basic. Aniline also was found ineffective both in the presence and absence of acid. The effective diamines of the invention are those listed above and specifically include, for example, meta-phenylenediamine, para-phenylenediamine, and 2,4-diamino toluene, which are preferred due to their low cost and availability. More than one of these diamines may be used in combination, but generally they are used alone. The diamines of the invention, in the presence of acid, are believed to complex, and form condensation products, with carbonyl impurities in esters; these products either precipitate from solution or may be separated from the ester by the described aqueous base treatment and washing and/or by distillation.

The $C_1$ to $C_4$ alkyl groups which may be used in the substituted positions of the phenylene diamines include, for example, methyl, ethyl, n- and iso-propyl, and n-, sec-, and iso-butyl groups. Acids which have been found effective in use with the diamines of the invention include those defined above and include, as examples, acrylic acid, methacrylic acid, poly-acrylic acid, propionic acid; methanesulfonic acid, and toluenesulfonic acid. The sulfonic acid may be used free or bound as the acid group of a strong acid ion exchange resin, such as in Amberlyst 15™ and Amberlyst 16™ ion exchange resins. Of these acids, acrylic and methacrylic acid are preferred due to their availability and compatibility with most unsaturated esters. The ratio of acid used is based on equivalents of total amine in the diamine and may be in large excess, up to 1500 equivalent ratio to the amine. A large ratio provides for an ester stream containing appreciable levels, for example, up to about 10 wt. % of the stream, of an acid such as acrylic acid. Preferred acid ratios are from about 5 to 1000, more preferred from about 10 to 800, equivalents of acid to equivalents of amine. When the acid chosen is immiscible in the ester or its solution, i.e. an acid such as a sulfonic acid bound to a polymeric support, as in a strong acid ion exchange resin, and thus affording a heterogeneous system, acid separation from the ester or ester solution is facilitated.

Temperatures for treatment of the ester range from about 20° C. to no greater than the normal boiling point of the ester and should be less than 150° C. Preferred treatment temperatures range from about 40° to 120° C. depending on the ester and not exceeding its normal boiling point. More preferred treatment temperature is in the range of 60° to 90° C. where phenylenediamine reaction rates with carbonyl compounds are efficient and ester decomposition and by-product formation rates are not high.

After sufficient time has been provided to allow complete reaction of the amine(s) with the carbonyl-containing impurities (up to 100 hours), the treated ester optionally may be contacted with an aqueous solution of a base selected from, for example, sodium carbonate, magnesium carbonate, sodium hydroxide, barium hydroxide, and similar bases. The aqueous base solution is of a composition such that there exists an equivalent excess of base in the range of at least 1.1 equivalents of base to each equivalent of added acid. Sufficient contact time is allowed for neutralization of the acid catalyst under stirred conditions. The treated ester, if it has been base neutralized, is then washed with water. Distillation of either the treated ester directly or the treated ester after base neutralizing and washing may be carried out in conventional manner to afford a highly purified ester substantially free of carbonyl-containing impurities.

EXAMPLES

The following examples are illustrative of the present invention. General Normal butyl acrylate ("BA") was chosen as a good representative of the α,β-unsaturated carboxylic esters of the invention. BA was obtained by acid-catalyzed esterification of acrylic acid with butyl alcohol, the acrylic acid (AA) having been prepared from propylene by oxidation. Fresh BA/AA stock solutions were prepared for test purposes each day by adding 1 part of acrylic acid to 99 parts of butyl acrylate. An analysis of a typical BA/AA stock solution sample showed the presence of 51 parts per million (ppm) of furfural and 38 ppm of benzaldehyde (PhCHO). Specific BA/AA stock solution analyses are noted as appropriate.

Analyses for carbonyl impurities were carried out by gas-liquid chromatography (glc) under calibrated conditions. Impurity levels as low as several ppm were detectable with an estimated precision, at levels under 100 ppm, of ±1 ppm.

Comparative Examples, C-1 and C-2

To a sample of the BA/AA stock solution was added an amine, as indicated, in an amount equivalent to a 10 fold molar ratio relative to the combined aldehyde molar amount. The amine-treated solution was then heated to 60 ° C. with stirring. After four hours at temperature, each solution was allowed to cool to 23 ° C. and was then analyzed for furfural and benzaldehyde content by glc. The results of the analyses for comparative examples using no amine, n-butyl amine (C-1) and aniline (C-2) are summarized in Table 1; they showed no or little (<10% ) reduction in carbonyl impurity and were thus ineffective in reducing carbonyl impurities, in contrast to known effectiveness of these amines in reducing carbonyl impurities in unsaturated acids.

TABLE 1

Treatment of BA/AA Stock Solution with None or 10-fold Molar Ratio of Amine at 60° C.

| Example No. | Amine | Residual Level of Carbonyl Impurity (ppm ± 1) | | % Reduction of Carbonyl Impurity | |
|---|---|---|---|---|---|
| | | Furfural | PhCHO | Furfural | PhCHO |
| | none | 51 | 38 | — | — |
| C-1 | Butylamine | 52 | 37 | 0 | 3 |
| C-2 | Aniline | 47 | 36 | 8 | 5 |

Comparative Examples C-3 to C-6

Comparative Examples 3 to 6 were treated in the same way as Comparative Examples 1 and 2, but in the absence of acid. The BA solution for these tests consisted of 100% by weight butyl acrylate and no added acid. The results of these comparative tests are summarized in Table 2 in which substantially no (<10%) reduction of carbonyl impurity occurred in the absence of acid, with the exception of C-3 Coutylamine). (Butylamine was effective in the absence of acid but very ineffective in the presence of acid (C-1); it also is known to contribute to by-product formation via Michael addition and transamidation reactions.)

TABLE 2

Treatment of Butyl Acrylate with None or 10-fold Molar Ratio
of Various Amines at 60° C. in the Absence of Acid

| Example No. | Amine | Residual Level of Carbonyl Impurity (ppm ± 1) Furfural | PhCHO | % Reduction of Carbonyl Impurity Furfural | PhCHO |
|---|---|---|---|---|---|
| | none | 51 | 38 | — | — |
| C-3 | n-Butyl-amine | 17 | 34 | 67 | 11 |
| C-4 | Aniline | 48 | 35 | 6 | 8 |
| C-5 | p-Phenylene-diamine | 49 | 35 | 4 | 5 |
| C-6 | 2,4-Diaminotoluene | 48 | 35 | 6 | 5 |

Examples 1 and 2

Examples 1 and 2 were handled identically as described for Comparative Examples 1 and 2, except the amines, para-phenylenediamine and 2,4diaminotoluene were used, respectively, and in the presence of acrylic acid in the BA/AA stock solution. The results of the effectiveness of these amines in reducing carbonyl impurities in the BA/AA stock solution are shown in Table 3. Substantial reductions of 39% and 61% of furfural, and 11% and 29% of benzaldehyde, respectively, were found under these test conditions.

TABLE 3

Treatment of BA/AA Stock Solution with None or a
10-fold Molar Ratio of Phenylene Diamines at 60° C.

| Example No. | Amine | Residual Level of Carbonyl Impurity (ppm ± 1) Furfural | PhCHO | % Reduction of Carbonyl Impurity Furfural | PhCHO |
|---|---|---|---|---|---|
| | none | 51 | 38 | — | — |
| 1 | p-Phenylene-diamine | 31 | 34 | 39 | 11 |
| 2 | 2,4-Diaminotoluene | 20 | 27 | 61 | 29 |

Example 3

Example 3 was treated in the same way as Examples 1 and 2 with the exception that the BA/AA stock solution was heated to 90° C. in the presence of 10 equivalents of 2,4 diaminotoluene. Due to the higher temperature, the precaution was taken of adding additional polymerization inhibitor (methyl ether of hydroquinone; MeHQ, 100 ppm) and sparging the monomer solution with air during the test period. Analysis of the stock solution showed that it contained 47 and 43 ppm of furfural and PhCHO respectively. Analysis of the mixture after treatment showed that it contained 6 ppm and <1 ppm of furfural and PhCHO respectively, a reduction of 87% and >98% of the respective aldehydes.

Comparative Examples C-7 to C-9 and Examples 4 to 7

To a sample of BA, acid was added (except for C-7, which contained no added acid) followed by an amount of meta-phenylenediamine (MPD) equivalent to a 10 fold (60 fold in Ex. 7) molar ratio relative to the combined aldehyde and protoanemonin (PTA) molar amount. Comparative Example (C-8) contained no MPD; Example 4 contained 10 wt. % AA. The respective solutions were stirred at room temperature for about 24 hours. Each solution then was analyzed for furfural and PhCHO content by glc. The resulting analyses of these comparative and working Examples are summarized in Table 4.

Analysis of the BA used in these tests, before treatment, showed 33, 8, and 6 ppm of furfural, PhCHO and PTA, respectively. The comparative example using no acid in the presence of 10 molar ratio MPD (C-7) shows little (<15%) reduction in carbonyl impurities (again demonstrating the ineffectiveness of this amine in the absence of acid). Comparative examples using no amine in the presence of typical amounts of acids (C-8 and C-9) also show little reduction in carbonyl impurities (<6%, demonstrating ineffectiveness of acid alone in the absence of certain amines). Examples 4–7, in which both MPD and representative acids are present, show substantial reduction in carbonyl content.

TABLE 4

Effect of Acid and MPD treatment of Carbonyl
Impurity-Containing BA at 23° C.

| Example No. | Amine[1] | Acid[2] | Residual Level of Carbonyl Impurity (ppm ± 1)[3] Furfural | PhCHO | % Reduction of Carbonyl Impurity Furfural | PhCHO |
|---|---|---|---|---|---|---|
| | none | none | 33 | 8 | — | — |
| C-7 | MPD | none | 30 | 7 | 9 | 13 |
| C-8 | none | $H_2SO_4$ | 32 | 8 | 3 | 0 |
| C-9 | none | IER | 31 | 8 | 6 | 0 |
| 4 | MPD | AA | 12 | 5 | 64 | 38 |
| 5 | MPD | $H_2SO_4$ | 6 | 5 | 82 | 38 |
| 6 | MPD | IER | 23 | 7 | 30 | 13 |
| 7 | MPD[4] | IER | 9 | 6 | 73 | 25 |

Notes: [1]Amine added in 10 molar ratio unless otherwise noted.
[2]Acid concentrations: $H_2SO_4$, 700 ppm; IER(sulfonic acid resin, 4.8 meq $H^+$/gram), 0.34 wt %; AA, 10 wt % of the BA/AA solution.
[3]Final level after stirring for one day.
[4]MPD added in 60 molar ratio.

Example 8

Treatment and Distillation of a
Carbonyl-Containing Butyl Acrylate

Analysis of a normal butyl acrylate sample showed the presence of 32 ppm of furfural and 8 ppm of PhCHO. An amount of MPD was added to the BA sample equivalent to a 10 fold molar ratio relative to the combined aldehyde molar level in the BA. A reaction solution (2.5 kg) was then prepared by adding 1 part of acrylic acid and 99 parts of the amine-admixed butyl acrylate, followed by stirring at ambient temperature. Analysis of a reaction solution sample after 24 hours showed the presence of 12 ppm of furfural and 5 ppm of PhCItO. Analysis of the stirred solution after three additional days showed <1 ppm of furfural and 2 ppm of PhCHO. The level of MPD was increased such that the total added was equivalent to a 20 fold molar ratio relative to the starting combined aldehyde molar level. Analysis after stirring for 24 hours showed no furfural detected and 2 ppm of PhCHO. The solution was then neutralized with sodium carbonate (1.2 molar ratio with respect to the added acrylic acid) and washed with de-ionized water three times. The organic layer was further purified by batch distillation in two portions in a 5 tray Oldershaw column, at a pressure of 20 mm Hg and with an air sparge of 20 cc/min. (to activate inhibitor). To reduce the extent of undesirable polymer formation, 1000 ppm of phenothiazine inhibitor was added prior to distillation. The forerun material for each portion was discarded and the remaining distillate collected and analyzed. In both batches, analyses of distillate samples showed no detectable (<1 ppm) acrylic acid, furfural, or PhCHO.

We claim:

1. A process for purifying an $\alpha,\beta$-unsaturated carboxylic acid ester containing carbonyl impurities, comprising:

a) admixing the $\alpha,\beta$-unsaturated carboxylic acid ester containing carbonyl impurities with:

1) from 1 to 100 molar ratio of a phenylenediamine, based upon moles of carbonyl impurities, the phenylenediamine having the formulas

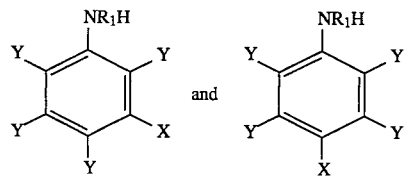

where
X is NR1R2 and
$R_1$, $R_2$, and Y are independently selected from hydrogen, $C_1$ to $C_4$ alkyl, phenyl, or naphthyl; and 2) from 1 to 1500 equivalent ratio, based on equivalents of the phenylenediamine, of an acid selected from a $C_1$ to $C_4$ carboxylic acid, a sulfonic acid, phosphoric acid, sulfuric acid, or mixtures thereof, to form a treated ester mixture; and b) holding the treated ester mixture up to 100 hours at a temperature of from 20° C. to 150° C.

2. The process of claim 1 further comprising the steps of aqueous base neutralizing and aqueous washing the treated ester mixture.

3. The process of claim 1 further comprising the step of distilling the treated ester mixture following the holding of step (b).

4. The process of claim 2 further comprising the step of distilling the treated ester mixture following the aqueous base neutralizing and aqueous washing steps.

5. The process of claim 1 wherein the $\alpha,\beta$-unsaturated carboxylic acid ester is selected from one or more ester of a $C_3$–$C_{10}$ carboxylic acid and a $C_1$–$C_{10}$ alcohol.

6. The process of claim 5 wherein the $\alpha,\beta$-unsaturated carboxylic acid ester is selected from an acrylic acid ester or a methacrylic acid ester.

7. The process of claim 6 wherein the $\alpha,\beta$-unsaturated carboxylic acid ester is selected from methyl acrylate, ethyl acrylate, butyl acrylate, methyl methacrylate or butyl methacrylate.

8. The process of claim 1 wherein the phenylene diamine is selected from meta-phenylenediamine, para-phenylenediamine, or 2,4-diamino toluene.

9. The process of claim 1 wherein the sulfonic acid is selected from methanesulfonic acid or toluenesulfonic acid.

10. The process of claim 1 wherein the sulfonic acid is the acid of a strong acid ion exchange resin.

* * * * *